United States Patent
Brown

(10) Patent No.: US 10,910,096 B1
(45) Date of Patent: Feb. 2, 2021

(54) AUGMENTED REALITY COMPUTING SYSTEM FOR DISPLAYING PATIENT DATA

(71) Applicant: Allscripts Software, LLC, Raleigh, NC (US)

(72) Inventor: Joshua Brown, Cary, NC (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 0 days.

(21) Appl. No.: 16/527,399

(22) Filed: Jul. 31, 2019

(51) Int. Cl.
*G16H 30/20* (2018.01)
*G06F 16/587* (2019.01)
*G06F 3/01* (2006.01)
*G16H 50/20* (2018.01)
*G16H 10/60* (2018.01)
*G06T 19/00* (2011.01)

(52) U.S. Cl.
CPC .............. *G16H 30/20* (2018.01); *G06F 3/01* (2013.01); *G06F 16/587* (2019.01); *G06T 19/006* (2013.01); *G16H 10/60* (2018.01); *G16H 50/20* (2018.01)

(58) Field of Classification Search
CPC ....................................................... G16H 30/20
See application file for complete search history.

(56) References Cited

U.S. PATENT DOCUMENTS

| 2002/0082498 | A1 | 6/2002 | Wendt et al. |
| 2007/0279187 | A1 | 12/2007 | Hekmatpour et al. |
| 2009/0074258 | A1 | 3/2009 | Cotgreave |
| 2011/0153341 | A1 | 6/2011 | Diaz |
| 2012/0233033 | A1 | 9/2012 | Calman et al. |
| 2014/0126770 | A1* | 5/2014 | Odessky ............... G06F 19/321 382/103 |
| 2014/0145915 | A1* | 5/2014 | Ribble ................... A61G 7/002 345/8 |
| 2015/0244903 | A1* | 8/2015 | Adams ............... H04N 5/23296 348/376 |
| 2016/0022226 | A1* | 1/2016 | Mayoras, Jr. ........ A61B 5/0022 340/286.07 |

FOREIGN PATENT DOCUMENTS

EP      2637593 A1    9/2013

* cited by examiner

*Primary Examiner* — Jitesh Patel
(74) *Attorney, Agent, or Firm* — Medley, Behrens & Lewis, LLC

(57) ABSTRACT

A computing system for displaying patient data in augmented reality (AR) is disclosed herein. An AR computing device worn by a healthcare worker captures an image indicative of a patient by way of a camera comprised by the AR computing device. The AR computing device transmits the image to an electronic health records application (EHR) executing on a server computing device. The EHR retrieves patient data for the patient responsive to identifying the patient based upon the image. Responsive to receiving the patient data from the EHR, the AR computing device presents the patient data on an AR display comprised by the AR computing device. The patient data is overlaid on the AR display with a view of surroundings of the healthcare worker as perceived by the healthcare worker through the AR display.

20 Claims, 9 Drawing Sheets

AUGMENTED REALITY COMPUTING SYSTEM FOR DISPLAYING PATIENT DATA

BACKGROUND

Electronic health records applications (EHRs) are computer-executable applications that are configured to assist healthcare workers with providing care to patients. EHRs are configured with functionality pertaining to patient intake, patient billing, insurance billing, prescription generation, maintaining a record of patient care over time, etc. EHRs are often used by healthcare workers at the point of care (i.e., at a time when the healthcare worker is providing care to a patient). For example, a healthcare worker may retrieve patient data from a patient record maintained by an EHR to relatively quickly ascertain problems being experienced by the patient, medications currently being taken by the patient, and so forth.

Conventionally, a computing device executing an EHR must receive an identifier for a patient and user credentials for a healthcare worker as manual input from the healthcare worker in order for the EHR to retrieve and display patient data for the patient to the healthcare worker. This is a cumbersome process for the healthcare worker and is computationally burdensome on the computing device as the computing device has to receive and process the input from the healthcare worker.

Additionally, the above-described conventional process is not well-suited for retrieving and displaying patient data for an ambulatory patient (i.e., a patient walking through a healthcare facility) that is encountered by the healthcare worker, as the healthcare worker must determine an identifier for the patient (e.g., ask the patient his or her name), access a computing device that executes an EHR, set forth input indicative of the patient to the EHR, and wait for the EHR to retrieve and display the patient data for the patient on a display of the computing device, at which point the patient may have moved to a different location in the healthcare facility than a location of the healthcare worker. If the patient data indicates that the patient is at risk (e.g., the patient data indicates that the patient should not walk unassisted and the patient is walking unassisted) and the patient has moved to a different location, the healthcare worker may be unable to properly warn the patient.

In other situations, patient data for a patient may be shown on a sign (e.g., a digital sign, a printed sign) posted on or around a door of a patient room of the patient or within the patient room. A healthcare worker may examine the sign to quickly ascertain the patient data for the patient. For instance, a sign on a door of a patient room may show patient data that indicates that the patient is at risk for falling and should not walk around unassisted. However, due to patient privacy concerns, the type of patient data that can be shown on the sign is limited. For instance, protected health information (PHI) of the patient may not be shown on the sign.

SUMMARY

The following is a brief summary of subject matter that is described in greater detail herein. This summary is not intended to be limiting as to the scope of the claims.

Disclosed herein are various technologies pertaining to displaying patient data in augmented reality (AR). With more specificity, an AR application is described herein that is configured to display patient data for a patient on an AR display as an overlay to surroundings of a healthcare worker as perceived by the healthcare worker through the AR display.

In operation, a healthcare worker located in a healthcare facility wears an AR computing device. The AR computing device comprises an AR display that is positioned over at least one eye of the healthcare worker. In an embodiment, the AR display comprises a transparent material or a semi-transparent material. The AR computing device also comprises various input components that enable the AR computing device to detect attributes of surroundings of the AR computing device (or enable the healthcare worker to provide input to the AR computing device), and hence the surroundings of the healthcare worker. For instance, the input components include a camera that is configured to capture images of the surroundings of the healthcare worker as the healthcare worker moves about the healthcare facility.

An AR application executing on the AR computing device captures an image that is indicative of a patient by way of the camera. In an example, the image may be a facial image of the patient. In another example, the image may be an image of a barcode that is assigned to a patient identifier for the patient. In yet another example, the image may be an image of text that is indicative of the patient (e.g., a medical records number (MRN) of the patient, a room number of the patient, etc.).

Responsive to capturing the image indicative of the patient, the AR application transmits the image to an electronic health records application (EHR) executing on a server computing device that is in network communication with the AR computing device. In an embodiment, the AR application may also transmit an identifier for the healthcare worker to the EHR. The EHR identifies the patient based upon the image (i.e., the EHR determines a patient identifier for the patient based upon the image). The EHR may additionally identify the patient based upon patient identification data that links patient identifiers used by the EHR to identify patients to images that are indicative of the patients. For instance, when the image indicative of the patient is a facial image of the patient and the patient identification data comprises facial images of patients that are labeled with patient identifiers for the patients, the EHR determines the patient identifier for the patient using computer-implemented facial recognition techniques that match the facial image of the patient received from the AR computing device to a facial image of the patient in the patient identification data.

Responsive to identifying the patient, the EHR retrieves patient data for the patient by executing a search based upon the patient identifier for the patient over patient data for patients. The search produces search results that include the patient data for the patient. Responsive to retrieving the patient data for the patient, the EHR transmits the patient data to the AR application. In an embodiment where the EHR has received an identifier for the healthcare worker, the EHR may also retrieve a list of tasks from the patient data that are to be performed by the healthcare worker with respect to the patient. In the embodiment, the EHR transmits the lists of tasks to the AR application.

Responsive to receiving the patient data from the EHR, the AR application presents the patient data on the AR display as an overlay to a view of surroundings of the healthcare worker as perceived by the healthcare worker through the AR display such that the patient data presented on the AR display appears to be part of the surroundings of the healthcare worker. The AR application may also receive the list of tasks from the EHR and may present the list of tasks on the AR display as part of the overlay.

The above-described technologies present various advantages over conventional technologies pertaining to retrieving and displaying patient data for patients. First, unlike conventional technologies, the technologies described above do not require an EHR to receive manual input from a healthcare worker each time the healthcare worker wishes to view patient data for a patient, and hence result in a reduced use of computing resources. Second, the technologies described above do not require the EHR to receive manual input from the healthcare worker in order for the EHR to retrieve a list of tasks that are to be performed by the healthcare worker with respect to the patient. Third, the technologies described above are well-suited for retrieving and displaying patient data for ambulatory patients in a healthcare facility. Fourth, the technologies described above enable protected health information (PHI) of the patient to be displayed to the healthcare worker without exposing the PHI to persons who are not authorized to view such data while at the same time not requiring the healthcare worker to set forth manual input to the EHR.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
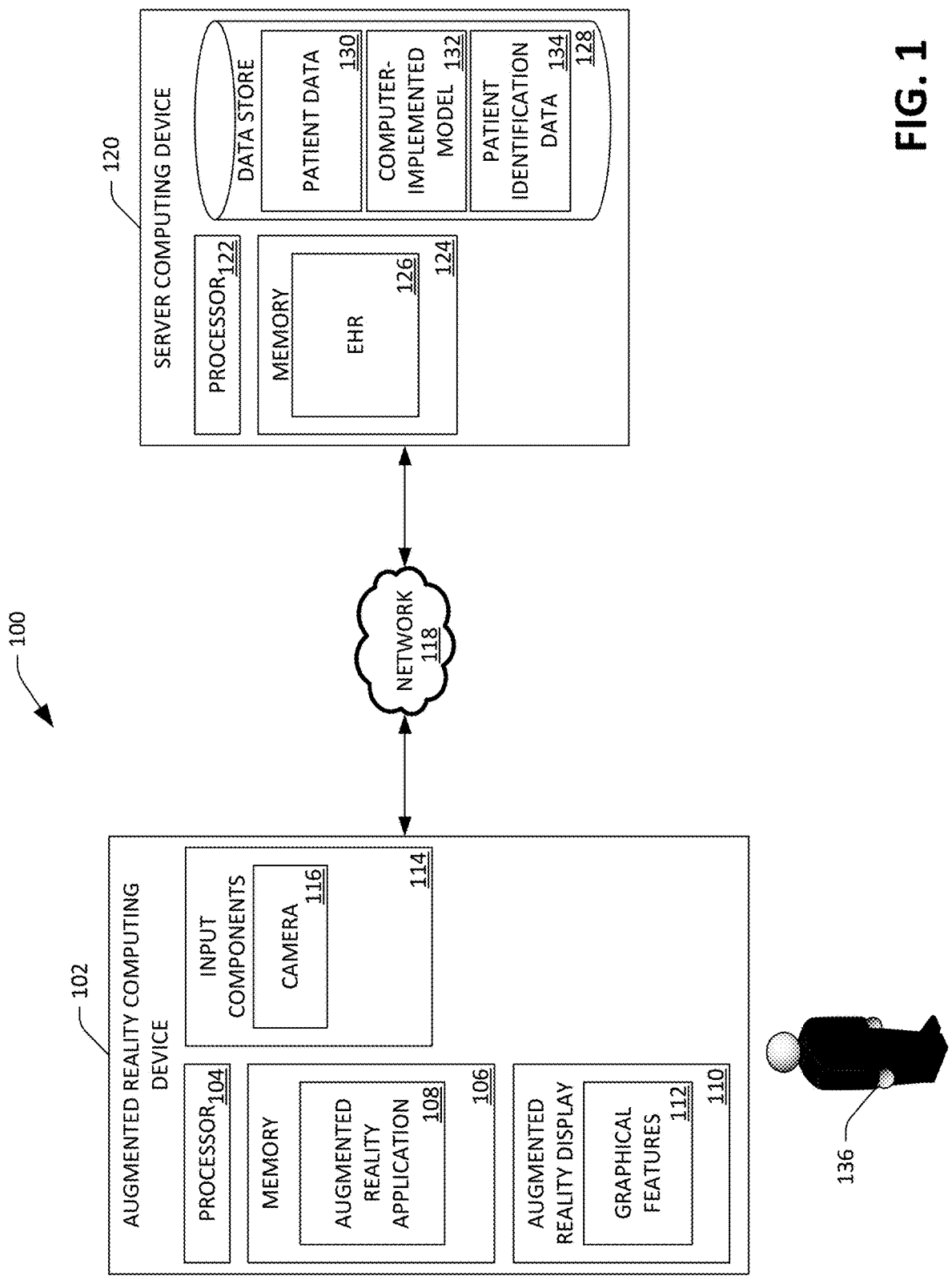
FIG. 1 is a functional block diagram of an exemplary computing system that facilitates displaying patient data in augmented reality.

Various technologies pertaining to displaying patient data in augmented reality (AR) are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component," "application," and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary computing system 100 that facilitates displaying patient data in AR is illustrated. The computing system 100 includes an AR computing device 102 that is worn by a healthcare worker 136 (e.g., a clinician, a nurse, etc.). For instance, in an embodiment, the AR computing device 102 may be a headset that is worn over the head of the healthcare worker 136.

The AR computing device 102 comprises a processor 104 and memory 106, wherein the memory 106 has an AR application 108 loaded therein. As will be described in greater detail below, the AR application 108 (when executed by the processor 104), is configured to display patient data for patients on an AR display comprised by the AR computing device 102. In an embodiment, the AR application 108 may be incorporated into a module of a client electronic health records application that executes on the AR computing device 102.

The AR computing device 102 further comprises an AR display 110, whereupon graphical features 112 may be presented thereon. For instance, the graphical features 112 may include patient data for a patient. The AR display 110 may be worn over at least one eye of the healthcare worker 136. For instance, the AR display 110 may be located 0.5 to 3 inches from the at least one eye of the healthcare worker 136.

In a first embodiment, the AR display 110 comprises a transparent material or a semi-transparent material (e.g., glass, clear plastic, etc.). As such, in the first embodiment, the healthcare worker 136 may perceive his/her surroundings through the AR display 110. Additionally, as will be described in greater detail below, the AR application 108 may cause the graphical features 112 to be presented on the AR display 110 as an overlay to the surroundings as viewed by the healthcare worker 136 through the AR display 110 such that the graphical features 112 appear to the healthcare worker 136 as part of the surroundings of the healthcare worker 136.

In a second embodiment, the AR display 110 comprises an opaque material (e.g., a liquid crystal display (LCD) screen, a light emitting diode (LED) screen, an organic LED (OLED) screen, etc.). As such, in the second embodiment, the graphical features 112 include first graphical features and second graphical features. The first graphical features correspond to surroundings of the healthcare worker 136 as perceived through a lens of at least one camera comprised by the AR computing device 102. The second graphical features correspond to features that are not physically part of the surroundings of the healthcare worker 136, but appear as such on the AR display 110. For instance, the second graphical features may include patient data for a patient that is overlaid with the first graphical features presented on the AR display 110.

The AR computing device 102 additionally comprises input components 114. The input components 114 enable the AR computing device 102 to detect attributes of surroundings of the AR computing device 102. The input components 114 may also enable the AR computing device 102 to receive input from the healthcare worker 136. The input components 114 include a camera 116 (or several cameras). As will be described in greater detail below, the camera 116 is configured to capture images of surroundings of the healthcare worker 136 as viewed from a perspective of eyes of the healthcare worker 136. The input components 114 may also include a microphone, hand-held controllers, buttons, video cameras, etc. Although not depicted in FIG. 1, the AR computing device 102 may also include speakers and a data store.

The computing system 100 additionally includes a server computing device 120 that is in communication with the AR computing device 102 by way of a network 118 (e.g., the Internet, intranet). The server computing device 120 comprises a processor 122 and memory 124, wherein the memory 124 has an electronic health records application (EHR) 126 loaded therein. The EHR 126 (when executed by the processor 122) is configured to perform a variety of tasks related to patient healthcare in a healthcare facility (e.g., patient intake, prescription generation, patient record creation and maintenance, etc.).

The server computing device 120 additionally includes a data store 128. The data store 128 comprises patient data 130 for patients, wherein the patient data 130 is maintained by the EHR 126. The patient data 130 may include clinical data for the patients, such as electronic health records, prescription records, claims data, patient/disease registries, health surveys data, clinical trials data, etc. Some or all of the patient data 130 may be protected health information (PHI). The patient data 130 may also include demographic data for the patients. Furthermore, the patient data 130 may include lists of tasks that are to be performed by healthcare workers with respect to the patients. The list of tasks may be scoped according to job functions of the healthcare workers. For instance, a list of tasks for a nurse may be different than a list of tasks for a physician. In an embodiment, the patient data 130 may include identifiers for healthcare workers that are authorized to view the patient data 130 (or portions thereof).

The data store 128 further comprises a computer-implemented model 132. In general, the computer-implemented model 132 is configured to take an image that is indicative of a patient captured by the camera 116 as input. The computer-implemented model 132 is configured to output, based upon the input, at least one value which the EHR 126 utilizes to identify a patient. In an example, the computer-implemented model 132 comprise nodes and edges that couple nodes in the computer-implemented model 132. Thus, for instance, the computer-implemented model 132 may be an artificial neural network (ANN), a Bayesian model, a deep neural network (DNN), a recurrent neural network (RNN), or the like. In another example, the computer-implemented model 132 may be or include a support vector machine (SVM) or other suitable classifier. When the computer-implemented model 132 comprises nodes and edges, each edge is assigned a learned weight, wherein the weight can be learned using a supervised or unsupervised learning procedure. In an embodiment, the computer-implemented model 132 may configured for optical character recognition (OCR).

The data store 128 additionally comprises patient identification data 134. The patient identification data 134 links patient identifiers used by the EHR 126 to identify patients to images that are indicative of the patients. In a first embodiment, the patient identification data 134 comprises facial images of patients and labels assigned to the facial images, wherein the labels are the patient identifiers for the patients. In a second embodiment, the patient identification data 134 comprises images of barcodes and labels assigned to the barcodes, wherein the labels are the patient identifiers for the patients. In a third embodiment, the patient identification data 134 comprises identifiers for rooms in a healthcare facility in which the patients are located and the patient identifiers for the patients in the rooms.

Figure 2:
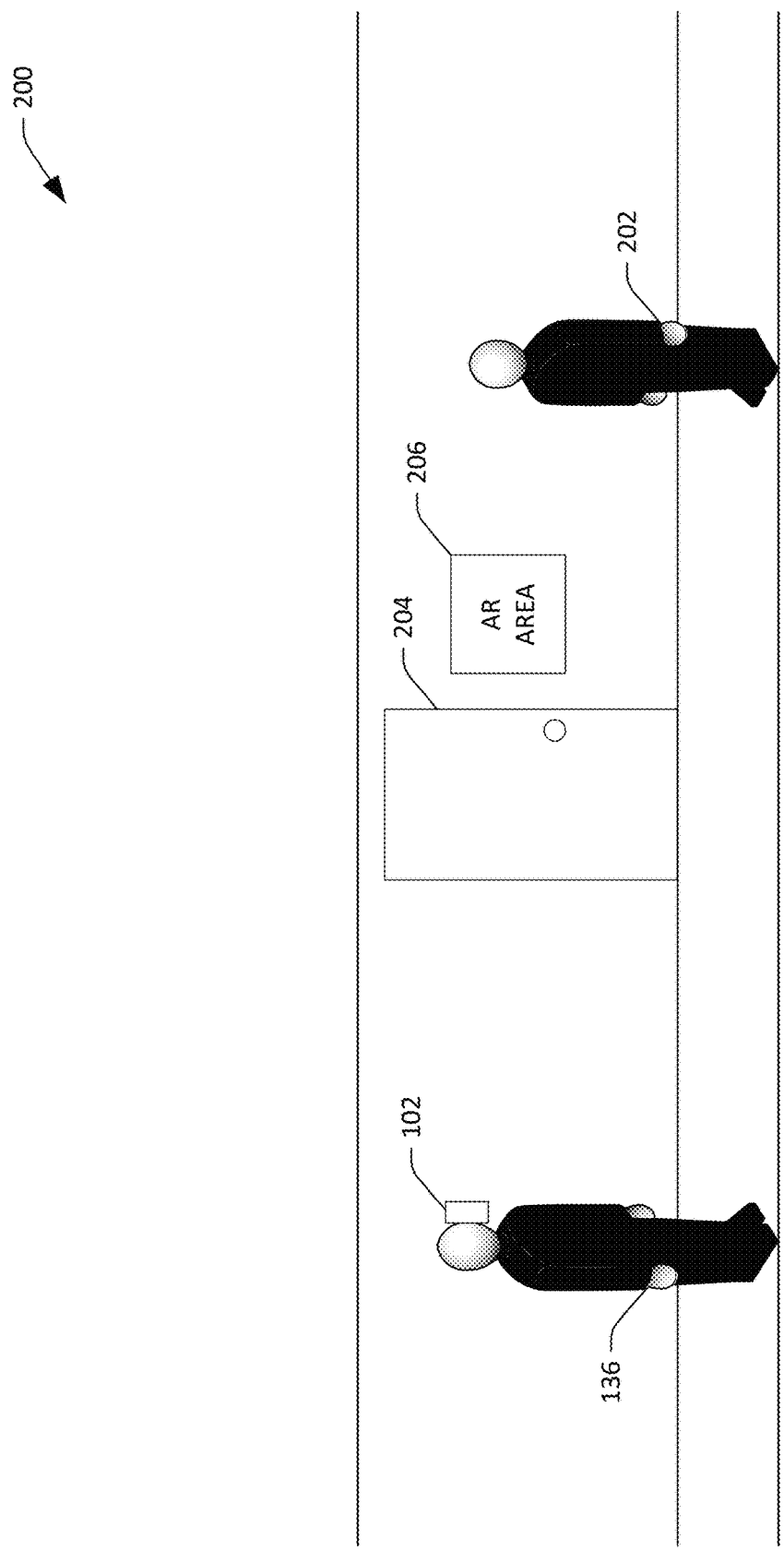
FIG. 2 depicts a side-view of a healthcare environment in a healthcare facility.

Turning now to FIG. 2, a cross-sectional view of a healthcare environment 200 in a healthcare facility is illustrated. For instance, the healthcare environment 200 may be a hallway in a healthcare facility. As shown in FIG. 2, the healthcare environment 200 includes the healthcare worker 136 that wears the AR computing device 102. The healthcare environment 200 also includes a patient 202 that is located in the healthcare facility. For instance, the patient 202 may be admitted to the healthcare facility. The healthcare environment 200 may include a door 204 to a patient room of the patient 202. The healthcare environment 200 may also include an AR area 206. Although the AR area 206 is depicted as being proximate to the door 204, it is to be understood that the AR area 206 may be located in other areas in the healthcare environment 200. For instance, the AR area 206 may be located on the door 204, inside the patient room, etc. The AR area 206 may include a marking (e.g., a barcode) that is indicative of a patient (e.g., the patient 202).

With reference now to FIGS. 1 and 2, operation of the computing system 100 is now set forth. As the healthcare work 136 moves about the healthcare environment 200 and/or the as the patient 202 moves about the healthcare environment 200, the patient 202 enters a field of view of a lens of the camera 116 comprised by the AR computing device 102. As such, the AR application 108 captures an image indicative of the patient 202 by way of the camera 116. For instance, the image may be facial image of the patient 202, an image of a barcode shown on a badge worn by the patient 202, an image of text on a badge worn by the patient 202, etc. Alternatively, the image indicative of the patient 202 may be an image of a barcode shown within the AR area 206. Responsive to capturing the image indicative of the patient 202, the AR application 108 transmits the image to the EHR 126.

Responsive to receiving the image indicative of the patient 202, the EHR 126 identifies the patient 202 based upon the image indicative of the patient 202. The EHR 126 may additionally identify the patient 202 based upon the patient identification data 134 and/or the computer-implemented model 132. More specifically, the EHR 126 may identify the patient 202 using a variety of computer-vision and classification techniques (e.g., facial recognition techniques, text-recognition techniques, barcode reading techniques, etc.).

In a first embodiment, the image indicative of the patient 202 is a facial image of the patient 202 and the patient identification data 134 comprises facial images of patients and labels assigned to the facial images, wherein the labels are patient identifiers for the patients. A facial image of the patient 202 is included in the facial images of the patients. In the first embodiment, the EHR 126 provides the facial image of the patient 202 as input to the computer-implemented model 132, and the computer-implemented model 132 outputs at least one value based upon the input. The EHR 126 utilizes the at least one value to identify the patient 202. More specifically, the EHR selects a facial image in the facial images comprised by the patient identification data 134 based upon the at least one value and identifies the patient 202 based upon a patient identifier that is labeled to the facial image in the facial images.

In a second embodiment, the image indicative of the patient is an image of a barcode assigned to the patient 202 and the patient identification data 134 comprises images of barcodes and labels assigned to the barcodes, wherein the labels are patient identifiers for patients. A barcode assigned to the patient 202 is included in the barcodes. In the second embodiment, the EHR 126 performs a comparison between the image of the barcode received from the AR application 108 and the barcodes comprised by the patient identification data 134. When the EHR 126 matches the image of the barcode to a barcode comprised by the patient identification data 134 (or finds a barcode in the barcode that matches the image of the barcode to a threshold similarity level), the EHR 126 determines a patient identifier for the patient 202 from a patient identifier assigned to the barcode in the barcodes. This process may also be aided by the computer-implemented model 132 in a process similar to the first embodiment described above where the image indicative of the patient 202 is a facial image of the patient 202.

In a third embodiment, the image indicative of the patient is an image of text (e.g., a medical record number (MRN) of the patient 202, a room number of the patient 202, etc.). The EHR 126 extracts the text from the image using computer-vision techniques. For instance, the EHR 126 provides the image of the text to the computer-implemented model 132 as input, and the computer-implemented model outputs computer-readable text based upon the input, wherein the computer-readable text is the patient identifier for the patient 202.

Responsive to identifying the patient 202 based upon the image indicative of the patient 202, the EHR 126 retrieves patient data for the patient 202 based upon the patient identifier for the patient 202. More specifically, the EHR 126 executes a search over the patient data 130 based upon the patient identifier for the patient 202. The search produces search results, wherein the search results include the patient data for the patient 202. The EHR 126 transmits the patient data for the patient 202 to the AR application 108.

Responsive to receiving the patient data for the patient 202 from the EHR 126, the AR application 108 presents the patient data for the patient 202 on the AR display 110 as part of the graphical features 112. The patient data is overlaid with a view of surroundings of the healthcare worker 136 as perceived by the healthcare worker 136 through the AR display 110 such that the patient data presented on the AR display 110 appears to be part of the surroundings of the healthcare worker 136.

Figure 3:
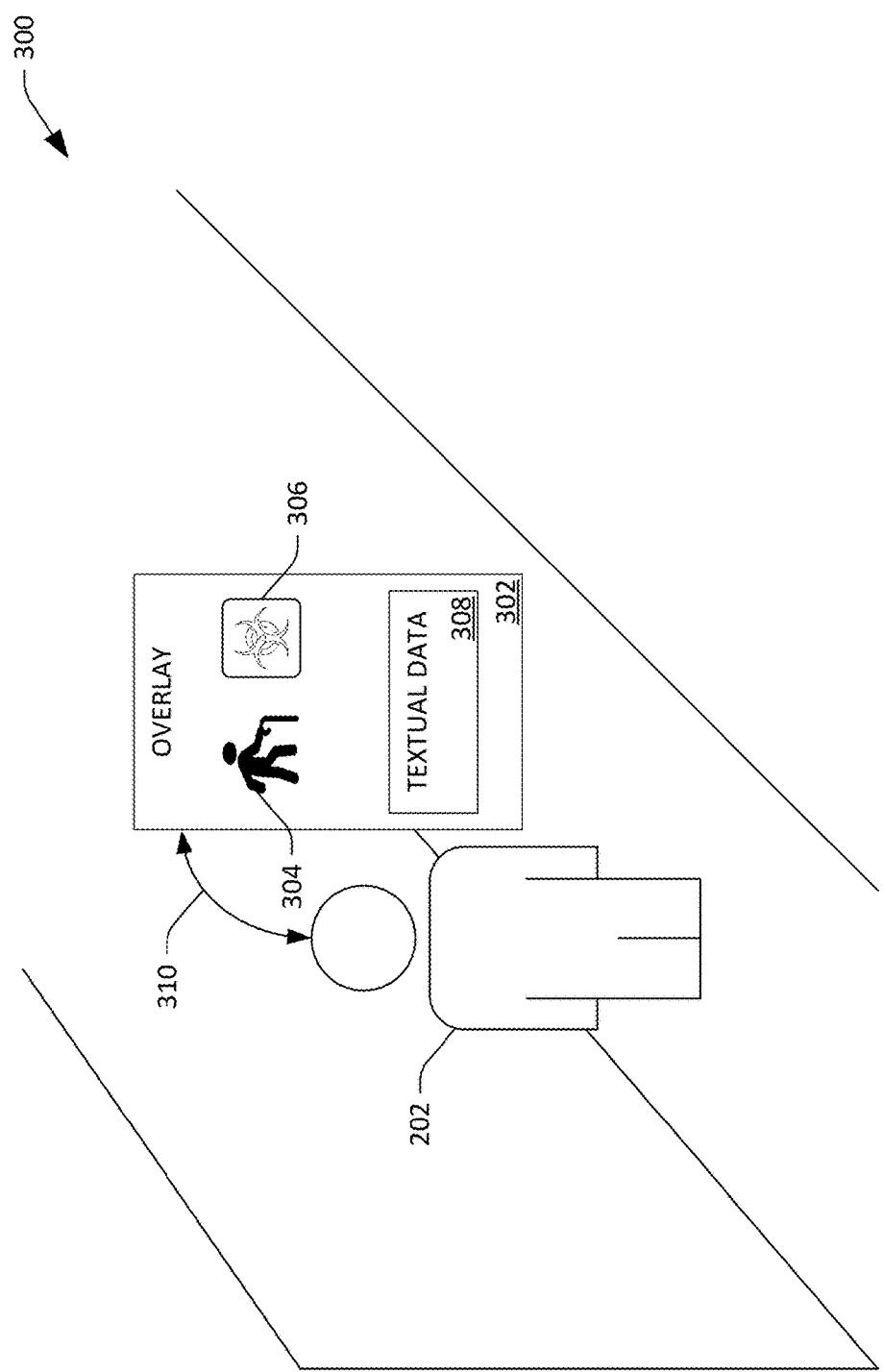
FIG. 3 depicts a head-on view of the healthcare environment depicted in FIG. 2 as perceived by a healthcare worker through an augmented reality display.

Referring now to FIG. 3, a head-on view 300 of the healthcare environment 200 depicted in FIG. 2 as seen through the AR display 110 of the AR computing device 102 after the AR application 108 receives the patient data for the patient 202 is illustrated. The view 300 includes the patient 202. The view 300 additionally includes an overlay 302 (presented on the AR display 110) that comprises the patient data for the patient 202 retrieved by the EHR 126. The overlay 302 includes a plurality of graphical symbols 304-306, each graphical symbol in the plurality of graphical symbols 304-306 indicative of a different patient attribute of the patient 202 in the patient data. For instance, the graphical symbol 304 may indicate that the patient 202 is at risk for falling and hence should not walk unassisted through the healthcare facility and the graphical symbol 306 may indicate that the patient 202 has an airborne, communicable disease and hence the patient 202 should not walk about the healthcare facility without taking proper prophylactic measures. Although two graphical symbols are depicted in FIG. 3, it is to be understood that the overlay 302 many include more than two graphical symbols (or less than two graphical symbols). The overlay 302 may also include textual data 308 for the patient 202. For instance, the textual data 308 may clinical data for the patient 202.

The view 300 may additionally include a marker 310 that indicates that the patient data displayed in the overlay 302 belongs to the patient 202. It is to be understood that the AR application 108 may cause the overlay 302 to "follow" the patient 202 on the AR display 110 as the patient 202 moves about the healthcare environment 200. For instance, the image indicative of the patient 202 may be a first image of the patient 202 and the patient data for the patient 202 may initially be located at a first position on the AR display 110 when the AR application 108 causes the AR computing device 102 to capture the first image by way of the camera 116. Subsequently, the AR application 108 causes the AR computing device 102 to capture a second image of the patient 202 by way of the camera 116. The AR application 108 detects that the patient 202 has moved from a first location in the surroundings of the healthcare worker 136 to a second location in the surroundings of the healthcare worker 136 based upon a comparison between the first image and the second image. The AR application 108 may reposition the patient data on the AR display 110 (as well as the marker 310) from the first position on the AR display 110 to a second position on the AR display 110 corresponding to the second location in the surroundings of the healthcare worker 136.

Figure 4:
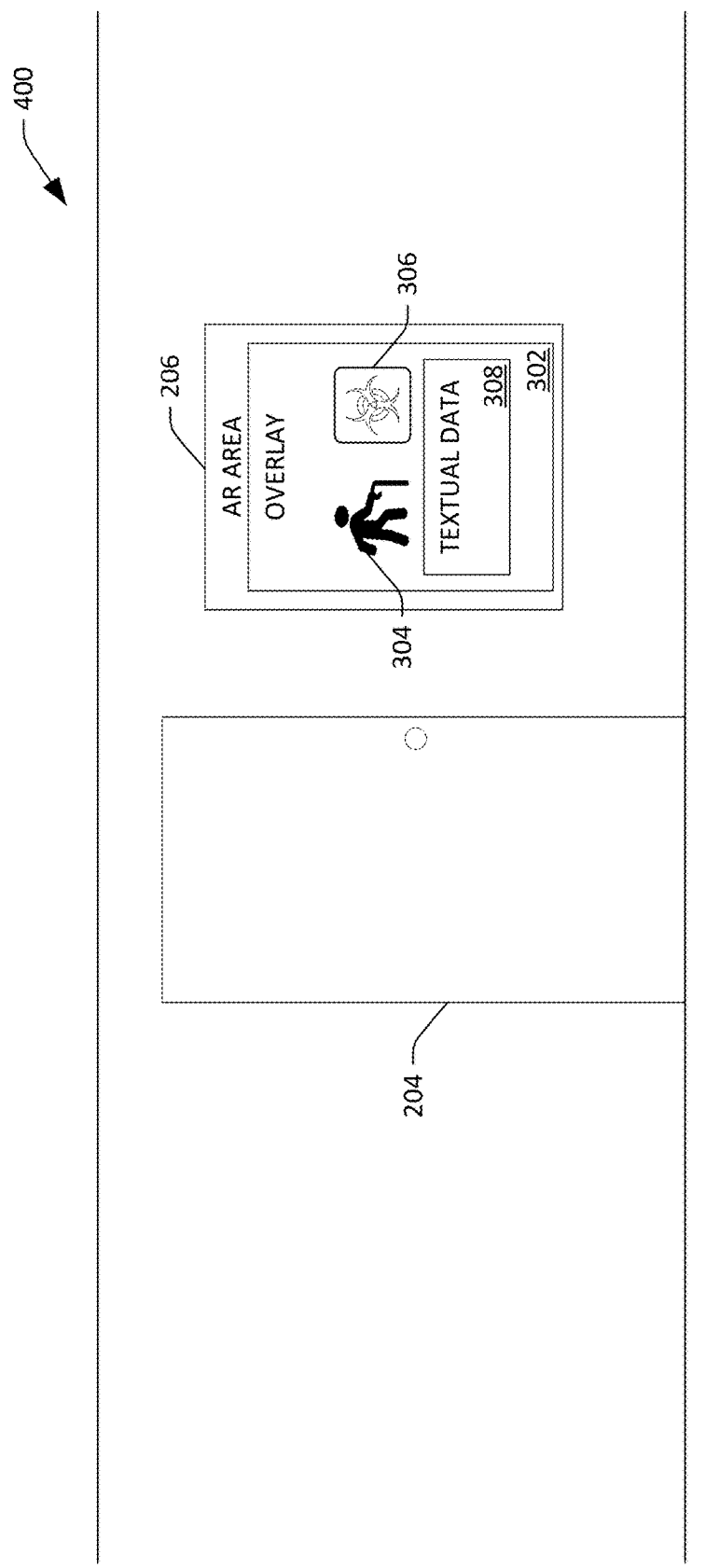
FIG. 4 depicts another head-on view of the healthcare environment depicted in FIG. 2 as perceived by a healthcare worker through an augmented reality display.

With reference now to FIG. 4, another head-on view 400 of the healthcare environment 200 depicted in FIG. 2 as seen through the AR display 110 of the AR computing device 102 after the AR application 108 receives the patient data for the patient 202 is illustrated. In the view 400, a field of view of a lens of the camera 116 of the AR computing device 102 is directed towards the AR area 206 (i.e., the healthcare worker 136 is looking at the AR area 206). The view 400 includes the overlay 302 described above, as well as the plurality of graphical symbols 304-306 and the textual data 308 described above in the description of FIG. 1. As shown in FIG. 4, the overlay 302 is presented on an area of the AR display 110 corresponding to the AR area 206 in the surroundings of the healthcare worker 136. The AR computing device 102 causes the overlay 302 to be presented on the area of the AR display 110 corresponding to the AR area 206 responsive to detecting that the field of view of the lens of the camera 116 is directed towards the AR area 206.

In an embodiment, the AR computing device 102 may transmit an identifier for the healthcare worker 136 to the EHR 126 prior to, concurrently with, or subsequent to transmitting the image indicative of the patient 202 to the sever EHR 126. In the embodiment, the EHR 126 may determine, based upon the identifier for the healthcare worker 136, that the healthcare worker 136 is authorized to view the patient data for the patient 202, that the healthcare worker 136 is authorized to view a subset of the patient data for the patient 202, or that the healthcare worker 136 is not authorized to view the patient data for the patient 202. When the EHR 126 determines that the healthcare worker 136 is authorized to view the patient data for the patient 202, the EHR 126 transmits the patient data for the patient 202 to the AR application 108 as described above. When the EHR 126 determines that the healthcare worker 136 is only authorized to view a subset of the patient data for the patient 202 (and not the entirety of the patient data for the patient 202), the EHR 126 retrieves the subset of the patient data for the patient 202 based upon the identifier for the healthcare worker 136 and the patient identifier. The EHR 126 transmits the subset of the patient data for the patient 202 to the AR application 108, whereupon the AR application 108 presents the subset of the patient data for the patient 202 on the AR display 110 as part of the graphical features 112. When the EHR 126 determines that the healthcare worker 136 is not authorized to view the patient data for the patient 202, the EHR 126 does not retrieve the patient data for the patient 202.

In an embodiment, the AR computing device 102 may transmit an identifier for the healthcare worker 136 to the EHR 126 prior to, concurrently with, or subsequent to transmitting the image that is indicative of the patient 202. In the embodiment, the EHR 126 determines that the healthcare worker 136 is not authorized to view the patient data for the patient 202 based upon the identifier for the healthcare worker 136. The EHR 126 also determines that the patient 202 is currently engaging in an activity that puts the patient 202 (or other patients) at risk based upon the image and the patient data for the patient 202. Responsive to determining that the healthcare worker 136 is not authorized to view the patient data for the patient 202 and that the patient 202 is engaging in the activity that puts the patient 202 (or other patients at risk), the EHR 126 may ascertain an identity of a second healthcare worker that is authorized to view the patient data for the patient 202. The EHR 126 may generate an alert comprising the patient data for the patient 202 and may transmit the patient data for the patient 202 to a computing device operated by the second healthcare worker, whereupon the computing device may present the alert to the second healthcare worker.

In an embodiment, the AR computing device 102 may transmit an identifier for the healthcare worker 136 to the EHR 126 prior to, concurrently with, or subsequent to transmitting the image that is indicative of the patient 202. In the embodiment, the EHR 126 retrieves a list of tasks that are to be performed by the healthcare worker 136 based upon the identifier for the healthcare worker 136 and the patient data for the patient 202. The list of tasks may be based upon a job function for healthcare worker 136. For instance, a first list of tasks displayed to a nurse wearing the AR computing device 102 may be different than a second list of tasks displayed to a physician wearing the AR computing device 102. The EHR 126 transmits the list of tasks to the AR computing device 102, whereupon the AR computing device 102 presents the list of tasks as part of the overlay 302 (e.g., as part of the textual data 308).

In an embodiment, the computing system 100 may utilize real time location services (RTLS) in order to facilitate displaying the patient data for the patient 202 in AR. For instance, the healthcare worker 136 and the patient 202 may have devices (e.g., mobile computing devices, radio-frequency identification (RFID) tags, etc.) on their persons that emit signals indicative of their locations within the healthcare facility. The signals may also be indicative of identifiers for the healthcare worker 136 and the patient 202. The EHR 126 may receive the signals and determine that the healthcare worker 136 and the patient 202 are within a vicinity of one another (e.g., in the same room, in the same hallway, etc.). The EHR 126 may then retrieve the patient data for the patient 202 and cause the patient data to be presented on the AR display 110 as described above. The embodiment may be useful in situations in which the AR computing device 102 has difficulty identifying the patient 202, such as situations in which a face of the patient 202 is fully or partially obscured.

Although operation of the computing system 100 has been described above with reference to the healthcare environment 200 depicted in FIG. 2, it is to be understood that the technologies described above are not limited to the healthcare environment 200 depicted in FIG. 2. For instance, the above-described technologies may display patient data on the AR computing device 102 when the healthcare worker 136 (and hence the AR computing device 102) are located in any location (e.g., a patient room, a lobby, a hallway, an examination area, a laboratory, etc.) inside a healthcare facility.

Although the AR computing device 102 has been described as a visual AR computing device that presents patient data in AR on the AR display 110, other possibilities are contemplated. For instance, the AR computing device 102 may emit audible sounds via a speaker or headphones comprised by the AR computing device 102, wherein the audible sounds correspond to the patient data (i.e., the AR computing device 102 may "read" the patient data to the healthcare worker 136).

Figure 5:
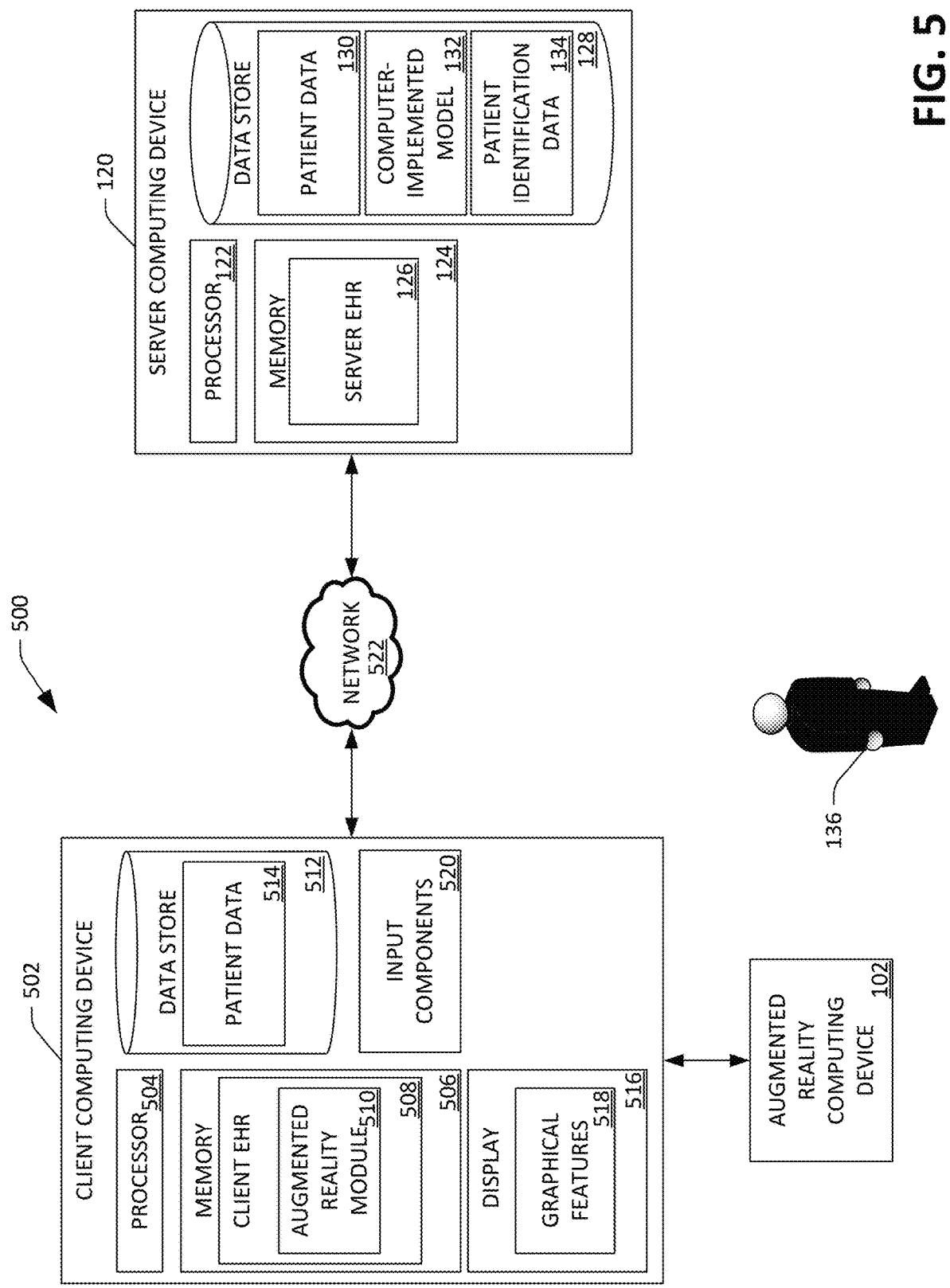
FIG. 5 is a functional block diagram of another exemplary computing system that facilitates displaying patient data in augmented reality.

Referring now to FIG. 5, an exemplary computing system 500 that facilitates displaying patient data in AR is illustrated. The computing system 500 includes the AR computing device 102 worn by the healthcare worker 136 as described above in the description of FIG. 1. The AR computing device 102 includes the components 104-116 described above in the description of FIG. 1. However, in the computing system 500, the AR application 108 (when executed by the processor 104) is not configured to directly communicate with the EHR 126 (now referred to as the server EHR 126 for clarity).

The computing system 500 additionally includes a client computing device 502 that is operated by the healthcare worker 136. In an embodiment, the client computing device 502 may be a tablet computing device or a smartphone. The client computing device comprises a processor 504 and memory 506, wherein the memory 506 has a client electronic health records application (client EHR) 508 loaded therein. The client EHR 508 (when executed by the processor 504) is configured to communicate with the server EHR 126 in order to perform programmatic tasks related to patients in a healthcare facility. The client EHR 508 includes an AR module 510 that is configured to communicate with the AR application 108 executing on the AR computing device 102. As such, the client computing device 502 is in communication with AR computing device 102.

The client computing device 502 may include a data store 512. The data store 512 may comprise patient data 514 about patients, wherein the patient data 514 is a subset of the patient data 130 described above in the description of FIG. 1. The client computing device 502 includes a display 516, whereupon graphical features 518 may be presented thereon. The client computing device 502 also includes input components 520 that enable the healthcare worker 136 to set forth input to the client computing device 502. For instance, the input components 520 may include a mouse, a keyboard, a touchscreen, a scroll wheel, a trackpad, a camera, a video camera, a microphone, etc.

The computing system 500 further includes the server computing device 120 described above in the description of FIG. 1. The server computing device 120 includes the components 122-134 described above in the description of FIG. 1. The server computing device 120 in communication with the client computing device 502 by way of a network 522 (e.g., the Internet, intranet).

The computing system 500 operates in a manner similar to that of the computing system 100 described above in the description of FIG. 1. However, in the computing system 500, the AR application 108 does not transmit images captured by the camera 116 directly to the server EHR 126, nor does the AR application 108 receive patient data for the patient 202 directly from the server EHR 126. Instead, the AR application 108 transmits the images captured by the camera 116 to the AR module 510 of the client EHR 508, whereupon the AR module 508 transmits the images to the server EHR 126. Likewise, the AR module 510 of the client EHR 508 receives the patient data for the patient 202 from the server EHR 126, whereupon the AR module 510 transmits the patient data for the patient 202 to the AR application 108 executing on the AR computing device 102. The AR application 108 then presents the patient data for the patient 202 on the AR display 110 as part of the graphical features 112 as described above.

Figure 6:
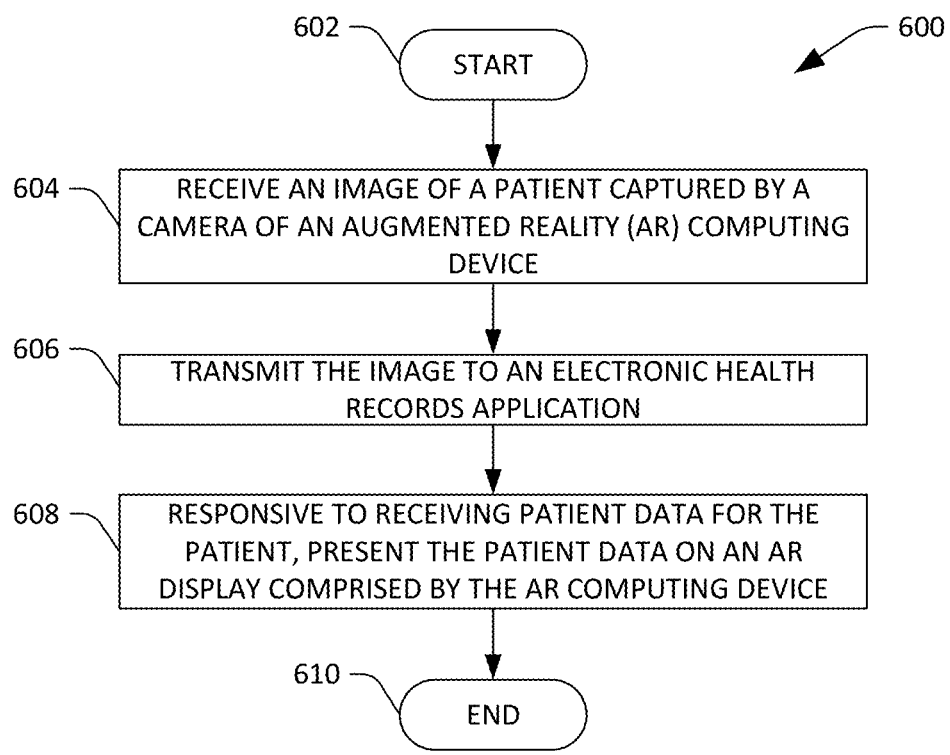
FIG. 6 is a flow diagram that illustrates an exemplary methodology performed by an augmented reality application that facilitates displaying patient data in augmented reality.
Figure 7:
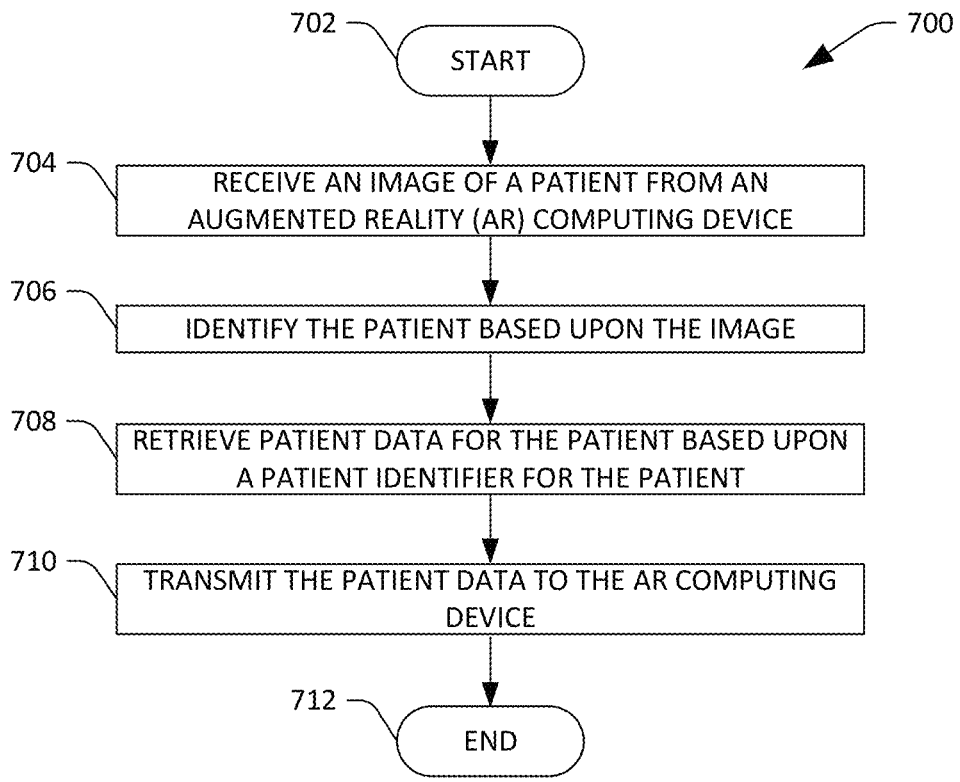
FIG. 7 is a flow diagram that illustrates an exemplary methodology performed by an electronic health records application that facilitates displaying patient data in augmented reality.
Figure 8:
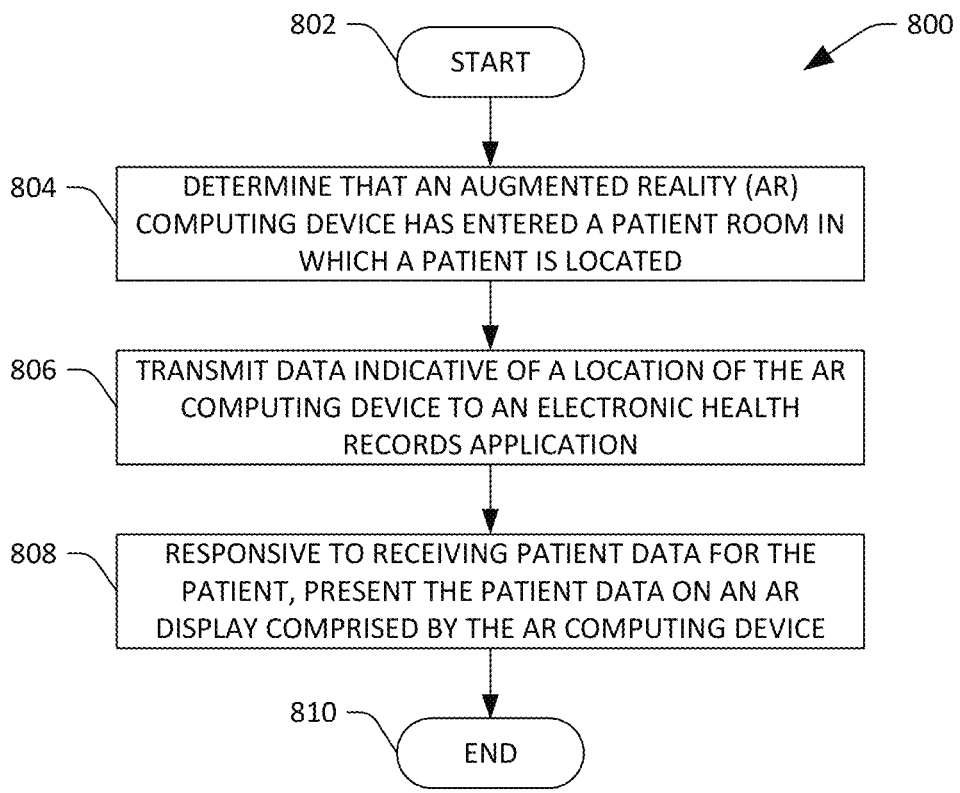
FIG. 8 is a flow diagram that illustrates an exemplary methodology performed by an augmented reality application that facilitates displaying patient data in augmented reality.

FIGS. 6-8 illustrate exemplary methodologies relating to displaying patient data in AR. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 6, a methodology 600 performed by an AR application executing on an AR computing device that facilitates displaying patient data in AR is illustrated. The methodology 600 begins at 602, and at 604, the AR application receives an image of a patient that has been captured by a camera comprised by the AR computing device. At 606, the AR application transmits the image to an EHR executing on a server computing device that is in network communication with the AR computing device. The EHR retrieves patient data for the patient responsive to identifying the patient based upon image. The EHR transmits the patient data to the AR application. At 608, responsive to receiving the patient data from the EHR, the AR application presents the patient data on the AR display. The patient data may be overlaid with a view of surroundings of the healthcare worker as perceived by the healthcare worker through the AR display such that the patient data presented on the AR display appears to be part of the surroundings of the healthcare worker. The methodology 600 concludes at 610.

Turning now to FIG. 7, a methodology 700 performed by an EHR executing on a server computing device that facilitates displaying patient data in AR is illustrated. The methodology 700 begins at 702, and at 704, the EHR receives an image of a patient from an AR application executing on an AR computing device that is in network communication with the server computing device. At 706, the EHR identifies the patient based upon the image, wherein the EHR maintains patient data for the patient. At 708, responsive to identifying the patient, the EHR retrieves the patient data for the patient based upon a patient identifier for the patient. At 710, the EHR transmits the patient data to the AR application, wherein the AR application presents the patient data on an AR display comprised by the AR computing device. The methodology 700 concludes at 712.

With reference now to FIG. 8, a methodology 800 performed by an AR application executing on an AR computing device that facilitates displaying patient data in AR is illustrated. The methodology 800 begins at 802, and at 804, the AR application determines that the AR computing device has entered a patient room of a patient. For instance, the AR application may determine that the AR computing device has entered the patient room based upon a signal emitted from a device in the patient room. At 806, responsive to determining that the AR computing device has entered the patient room, the AR application transmits data that is indicative of a location of the AR computing device to an EHR executing on a server computing device that is in network communication with the AR computing device. The EHR identifies the patient based upon the data. For instance, the EHR may determine an identity of the patient room based upon the data and the EHR may identify the patient based upon the identity of the patient room. Responsive to identifying the patient, the EHR retrieves patient data for the patient and transmits the patient data to the AR application. At 808, responsive to receiving the patient data from the EHR, the AR application presents the patient data on an AR display comprised by the AR computing device. The methodology 800 concludes at 810.

Figure 9:
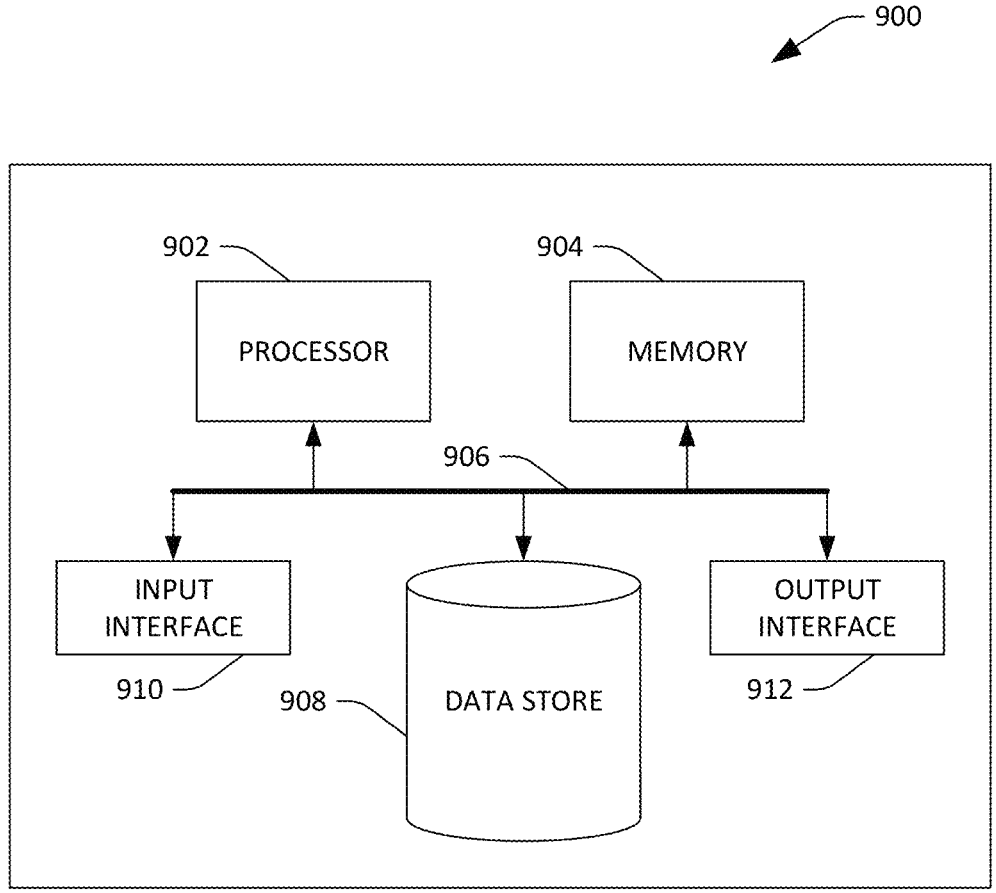
FIG. 9 is an exemplary computing system.

Referring now to FIG. 9, a high-level illustration of an exemplary computing device 900 that can be used in accordance with the systems and methodologies disclosed herein is illustrated. For instance, the computing device 900 may be used in a computing system that displays patient data for a patient in AR. By way of another example, the computing device 900 can be used in a system that retrieves patient data for a patient from a data store based upon a patient identifier for the patient. The computing device 900 includes at least one processor 902 that executes instructions that are stored in a memory 904. The instructions may be, for instance, instructions for implementing functionality described as being carried out by one or more components discussed above or instructions for implementing one or more of the methods described above. The processor 902 may access the memory 904 by way of a system bus 906. In addition to storing executable instructions, the memory 804 may also store patient data, computer-implemented models, patient identification data, user credentials for healthcare workers, images indicative of patients, etc.

The computing device 900 additionally includes a data store 908 that is accessible by the processor 902 by way of the system bus 906. The data store 908 may include executable instructions, patient data, computer-implemented machine learning models, patient identification data, user credentials for healthcare workers, images indicative of patients, etc. The computing device 900 also includes an input interface 910 that allows external devices to communicate with the computing device 900. For instance, the input interface 910 may be used to receive instructions from an external computer device, from a user, etc. The computing device 900 also includes an output interface 912 that interfaces the computing device 900 with one or more external devices. For example, the computing device 900 may display text, images, etc. by way of the output interface 912.

It is contemplated that the external devices that communicate with the computing device 900 via the input interface 910 and the output interface 912 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 900 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 900 may be a distributed system. Thus, for instance, several devices may be in communication by way of a network connection and may collectively perform tasks described as being performed by the computing device 900.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. An augmented reality (AR) computing device worn over at least one eye of a healthcare worker, the AR computing device comprising:
    a processor;
    a camera;
    an AR display; and
    memory storing an AR application that, when executed by the processor, causes the processor to perform acts comprising:
        capturing an image indicative of a patient by way of the camera;
        transmitting the image to an electronic health records application (EHR) executing on a server computing device that is in network communication with the AR computing device, wherein the EHR retrieves patient data for the patient responsive to identifying the patient based upon the image, wherein the patient data indicates that the patient has an airborne, communicable disease, wherein the EHR transmits the patient data to the AR application; and
        responsive to receiving the patient data, presenting the patient data on the AR display as an overlay to a view of surroundings of the healthcare worker as perceived by the healthcare worker through the AR display such that the patient data presented on the AR display appears to be part of the surroundings of the healthcare worker.

2. The AR computing device of claim 1, the acts further comprising:
    prior to presenting the patient data on the AR display and subsequent to transmitting the image to the EHR, detecting that a lens of the camera is directed towards an AR area in the surroundings of the healthcare worker, wherein the patient data is presented on an area of the AR display corresponding to the AR area in the surroundings of the healthcare worker.

3. The AR computing device of claim 1 the acts further comprising:
prior to receiving the patient data from the EHR, transmitting an identifier for the healthcare worker to the EHR, wherein the EHR determines whether the healthcare worker is authorized to view the patient data based upon the identifier for the healthcare worker, wherein the EHR transmits the patient data to the AR application when the EHR determines that the healthcare worker is authorized to view the patient data.

4. The AR computing device of claim 1, wherein the patient data comprises a plurality of graphical symbols, each graphical symbol in the plurality of graphical symbols indicative of a different patient attribute of the patient.

5. The AR computing device of claim 1, wherein the patient data indicates that the patient is at risk for falling.

6. The AR computing device of claim 1, wherein the image indicative of the patient is an image of a barcode that is assigned to the patient.

7. The AR computing device of claim 6, wherein identifying the patient based upon the image comprises:
comparing the image of the barcode to images of barcodes accessible to the EHR, wherein each barcode in the barcodes is assigned to a different patient identifier for a different patient, the barcode is included in the barcodes;
matching the barcode in the image to a barcode in the barcodes; and
determining a patient identifier for the patient based upon a patient identifier assigned to the barcode in the barcodes, wherein the EHR retrieves the patient data for the patient using the patient identifier.

8. The AR computing device of claim 1, the acts further comprising:
transmitting an identifier for the healthcare worker to the EHR, wherein the EHR retrieves a list of tasks to be performed by the healthcare worker with respect to the patient based upon the identifier for the healthcare worker and the patient data for the patient, wherein the EHR transmits the list of tasks to the AR application; and
presenting the list of tasks on the AR display as part of the overlay.

9. The AR computing device of claim 1, wherein the EHR determines that the patient is at risk based upon the patient data and the image, wherein the EHR determines that the healthcare worker is not authorized to view the patient data based upon an identifier for the healthcare worker received by the EHR from the AR computing device, wherein the EHR transmits an alert to a computing device operated by a second healthcare worker, wherein the second healthcare worker is authorized to view the patient data, wherein the computing device presents the alert to the second healthcare worker.

10. The AR computing device of claim 1, wherein the patient is located at a first location in the surroundings of the healthcare worker when the AR computing device captures the image indicative of the patient, wherein the image indicative of the patient is a first image of the patient, wherein the patient data is located at a first position on the AR display, the acts further comprising:
capturing a second image of the patient by way of the camera;
detecting that the patient has moved from the first location in the surroundings of the healthcare worker to a second location in the surroundings of the healthcare worker based upon a comparison between the first image and the second image; and
repositioning the patient data on the AR display from the first position on the AR display to a second position on the AR display, the second position corresponding to the second location in the surroundings of the healthcare worker.

11. A method executed by a processor of an augmented reality (AR) computing device worn by a healthcare worker while the processor executes an AR application, the method comprising:
receiving an image of a patient that has been captured by a camera comprised by the AR computing device;
transmitting the image to an electronic health records application (EHR) executing on a server computing device that is in network communication with the AR computing device, wherein the EHR retrieves patient data for the patient responsive to identifying the patient based upon the image, wherein the patient data indicates that the patient has an airborne, communicable disease, wherein the EHR transmits the patient data to the AR application; and
responsive to receiving the patient data from the EHR, presenting the patient data on an AR display comprised by the AR computing device.

12. The method of claim 11, wherein the EHR has access to images of patients admitted to a healthcare facility in which the healthcare worker and the patient are located, wherein the images are labeled with patient identifiers, wherein the EHR provides the image of the patient received from the AR application as input to a computer-implemented model, wherein the computer-implemented model outputs at least one value based upon the input, wherein the EHR selects an image in the images based upon the at least one value, wherein the EHR identifies the patient based upon the patient identifier that is labeled to the image in the images, wherein the image of the patient is a facial image of the patient, wherein the images of the patients are facial images of the patients.

13. The method of claim 11, further comprising:
prior to receiving the patient data from the EHR, transmitting an identifier for the healthcare worker to the EHR, wherein the EHR determines whether the healthcare worker is authorized to view the patient data based upon the identifier for the healthcare worker, wherein the EHR transmits the patient data to the AR application when the EHR determines that the healthcare worker is authorized to view the patient data.

14. The method of claim 11, wherein the AR display comprises a transparent material or a semi-transparent material.

15. The method of claim 11, wherein the patient data is overlaid with a view of surroundings of the healthcare worker as perceived by the healthcare worker through the AR display such that the patient data presented on the AR display appears to be part of the surroundings of the healthcare worker.

16. The method of claim 11, further comprising:
transmitting an identifier for the healthcare worker to the EHR, wherein the EHR retrieves a list of tasks to be performed by the healthcare worker with respect to the patient based upon the identifier for the healthcare worker and the patient data for the patient, wherein the EHR transmits the list of tasks to the AR application; and presenting the list of tasks on the AR display.

17. The method of claim 11, further comprising:

prior to presenting the patient data on the AR display and subsequent to transmitting the image to the EHR, detecting that a lens of the camera is directed towards an AR area in the surroundings of the healthcare worker, wherein the patient data is presented on an area of the AR display corresponding to the AR area in the surroundings of the healthcare worker.

18. The method of claim 11, wherein the patient data comprises a plurality of graphical symbols, each graphical symbol in the plurality of graphical symbols indicative of a different patient attribute of the patient.

19. A computing device, comprising:

a processor; and memory storing an augmented reality (AR) application that, when executed by the processor, causes the processor to perform acts comprising:

receiving an image of a patient captured by a camera comprised by an AR computing device worn over at least one eye of a healthcare worker;

causing the image to be transmitted to an electronic health records application (EHR) executing on a server computing device that is in network communication with the computing device, wherein the EHR retrieves patient data for the patient responsive to identifying the patient based upon the image, wherein the patient data indicates that the patient has an airborne, communicable disease, wherein the EHR transmits the patient data to the AR application; and responsive to receiving the patient data from the EHR, causing the patient data to be presented on an AR display comprised by the AR computing device worn by the healthcare worker, wherein the patient data is overlaid with a view of surroundings of the healthcare worker as perceived by the healthcare worker through the AR display such that the patient data presented on the AR display appears to be part of the surroundings of the healthcare worker.

20. The computing device of claim 19, wherein the patient data comprises a plurality of graphical symbols, each graphical symbol in the plurality of graphical symbols indicative of a different patient attribute of the patient.

* * * * *